US006662128B2

(12) United States Patent
Barbour et al.

(10) Patent No.: US 6,662,128 B2
(45) Date of Patent: Dec. 9, 2003

(54) NORMALIZED-CONSTRAINT ALGORITHM FOR MINIMIZING INTER-PARAMETER CROSSTALK IN IMAGING OF SCATTERING MEDIA

(75) Inventors: Randall L. Barbour, Glen Head, NY (US); Harry L. Graber, Brooklyn, NY (US); Yaling Pei, Morris Plains, NJ (US)

(73) Assignee: The Research Foundation of State University of New York, Albany, NY (US)

( * ) Notice: Subject to any disclaimer, the term of this patent is extended or adjusted under 35 U.S.C. 154(b) by 62 days.

(21) Appl. No.: 10/052,609

(22) Filed: Jan. 18, 2002

(65) Prior Publication Data

US 2003/0139893 A1 Jul. 24, 2003

(51) Int. Cl.[7] .......................... G01N 21/00; G06F 19/00
(52) U.S. Cl. ........................ 702/84; 702/104; 702/127; 356/342; 356/435
(58) Field of Search ............................. 702/85, 94, 104, 702/127; 356/39, 43, 45, 435–438, 342

(56) References Cited

U.S. PATENT DOCUMENTS

| | | | | |
|---|---|---|---|---|
| 5,137,355 A | | 8/1992 | Barbour et al. | 356/342 |
| 6,081,322 A | * | 6/2000 | Barbour | 356/73.1 |
| 6,529,846 B2 | * | 3/2003 | Barbour | 702/104 |
| 6,549,284 B1 | * | 4/2003 | Boas et al. | 356/446 |

FOREIGN PATENT DOCUMENTS

| | | | | |
|---|---|---|---|---|
| WO | WO 01/20305 A1 | 3/2001 | | G01N/21/00 |
| WO | WO 01/20306 A1 | 3/2001 | | G01N/21/00 |
| WO | WO 01/20307 A1 | 3/2001 | | G01N/21/00 |
| WO | WO 01/20546 A2 | 3/2001 | | |

OTHER PUBLICATIONS

J. Chang, H.L. Graber, R.L. Barbour and R. Aronson., "Recovery of optical cross–section perturbations in dense–scattering media by transport–theory–based imaging operators and steady–state simulated data", Appl. Opt., vol. 35, No. 20., Jul. 10, 1996.

C. H. Schmitz, M. Löcker, J. Lasker, A. H. Hielscher, and R. L. Barbour, "Performance characteristics of silicon photo-diode (SiPD) based instrument for fast function optical tomography," Proc. SPIE 4250, San Jose, CA, in press, (2000).

Y. Pei, H. L. Graber and R L. Barbour, "Influence of systematic errors in reference states on image quality and on stability of derived information for DC optical imaging,", Appl. Opt., vol. 40, No. 31, Nov. 1, 2001.

G. Landis, S. Blattman, T. Panetta, C. H. Schmitz, H. L. Graber. Y. Pei, and R. L. Barbour, "Clinical applications of dynamic optical tomography in vascular disease," Proc. SPIE 4250, San Jose, CA, in press, (2001).

(List continued on next page.)

*Primary Examiner*—Kamini Shah
(74) *Attorney, Agent, or Firm*—Scully, Scott, Murphy & Presser

(57) ABSTRACT

A method and system for minimizing inter-coefficient crosstalk in imaging the internal properties of a scattering medium. The method and system minimizing inter-coefficient. crosstalk in image reconstruction by solving a system of linear perturbation equations with the use of relative detector values, weight matrix scaling, and constraints based on either the know or unknown direction of the perturbations in the medium's properties. The constraint being either (1) positive or negative corresponding to the direction of a known perturbations, or (2) solving the system of equations with both positive and negative constraints and summing the results where the direction of the perturbations are unknown. The advantages of the inventive method and system result in effective isolation of absorption and scattering coefficient variations, even for complex combinations of perturbations in these coefficients.

42 Claims, 6 Drawing Sheets

(4 of 6 Drawing Sheet(s) Filed in Color)

OTHER PUBLICATIONS

H. L. Graber, Y. Pei and R. L. Barbour, "Imaging of spatiotemporal coincident states by dynamic optical tomography," Proc. SPIE 4250, San Jose, CA, in press, (2001).

R. L. Barbour, H.L. Graber, Y. Pei, S. Zhong, and C.H. Schmitz, "Optical tomographic imaging of dynamic features of dense–scattering media", J. Opt. Soc. Am. A, vol. 18, No. 12, Dec. 2001.

B.J. Hoenders, "Existence of invisible nonscattering objects and nonradiating sources", J. Opt. Soc. Am. A, vol. 14, No. 1, Jan. 1997.

C. Hebden, S. R. Arridge and M. Schweiger, "Investigation of alterative data types for time–resolved optical tomography," *Trends in Optics and Photonics vol. 21, Advances in Optical Imaging and Photon Migration*, James G. Fujimoto and Michael S. Patterson, eds. (Optical Society of America, Washington, DC 1998).

S. R. Arridge and W. R. B. Lionheart, "Nonuniqueness in diffusion–based optical tomography", Opt. Lett., vol. 23, No. 11, Jun. 1, 1998.

H. Dehghani, D. T. Delpy and S. R. Arridge, "Photon migration in non–scattering tissue and the effects on image reconstruction", Phys. Med. Biol., vol. 44, 1999.

T.O. McBride, B. W. Pogue, U.L. Österberg, and K.D. Paulsen, "Separation of absorption and scattering heterogeneities in NIR tomographic imaging of tissue," in Biomedical Topical Meetings, OSA Technical Digest (Optical Society of America, Washington, D.C., 2000).

N. Iftimia and H. Jiang, "Quantitative optical image reconstruction of turbid media by use of direct–current measurements", Appl Opt, vol. 39, No. 28, Oct. 1, 2000.

Y. Xu, N. Iftimia, H. Jiang, L. Key, M. Bolster, "Imaging of in vitro and in vivo bones and joints with continuous–wave diffuse optical tomography", Opt Express, vol. 8, No. 7, Mar. 26, 2001.

\* cited by examiner

NORMALIZED-CONSTRAINT ALGORITHM FOR MINIMIZING INTER-PARAMETER CROSSTALK IN IMAGING OF SCATTERING MEDIA

This invention was made with U.S. Government support under NIH grant number R01 CA66184. The U.S. Government has certain rights in the invention.

FIELD OF THE INVENTION

The invention relates to the field of imaging in a scattering medium, and in particular to a method of minimizing inter-parameter crosstalk in imaging the internal properties of a scattering medium.

BACKGROUND

Imaging of a scattering medium relates generally to an imaging modality for generating an image of the spatial distribution of properties (such as the absorption or scattering coefficients) inside a scattering medium through the introduction of energy into the medium and the detection of the scattered energy emerging from the medium. These systems and methods are in contrast to projection imaging systems, such as x-ray. X-ray systems, for example, measure and image the attenuation or absorption of energy traveling a straight line path between the x-ray energy source and a detector, and not scattered energy. Whether the energy is primarily highly scattered or primarily travels a straight line path is a function of the wavelength of the energy and medium it is traveling through.

Imaging based on scattering techniques permits the use of new energy wavelengths for imaging features of the human body, earth strata, atmosphere and the like that were unable to be imaged using projection techniques and wavelengths. For example, x-ray projection techniques may be adept at imaging bone structure and other dense objects, but are relatively ineffective at distinguishing and imaging blood oxygenation levels. This is because the absorption coefficient of blood does not vary significantly with blood oxygenation, at x-ray wavelengths. However, infrared energy can identify the spatial variations in blood volume and blood oxygenation levels because the absorption coefficient at this wavelength is a function of hemoglobin states. Other structures and functions can be identified by variations or changes in the scattering coefficient of tissue exposed to infrared energy, such as muscle tissue during contraction, and nerves during activation. These structures could not be imaged by projection techniques because projection techniques are not effective in measuring variations in scattering coefficients. These measures, obtainable through imaging based on scattering techniques, such as optical tomography, have considerable potential value in diagnosing a broad range of disease processes.

A typical system for imaging based on scattered energy measures, includes at least one energy source for illuminating the medium and at least one detector for detecting emerging energy. The energy source is selected so that it is highly scattering in the medium to be imaged. The source directs the energy into the target scattering medium and the detectors on the surface of the medium measure the scattered energy as it exits. Based on these measurements, a reconstructed image of the internal properties of the medium is generated.

The reconstruction is typically carried out using "perturbation methods". These methods essentially compare the measurements obtained from the target scattering medium to a known reference scattering medium. The reference medium may be a physical or fictitious medium which is selected so that it has properties that are as close as possible to those of the medium to be imaged. Selecting a reference medium is essentially an initial guess of the properties of the target. In the first step of reconstruction, a "forward model" is used to predict what the detector readings would be for a particular source location based on the known internal properties of the reference medium. The forward model is based on the transport equation or its approximation, the diffusion equation, which describes the propagation of photons through a scattering medium. Next, a perturbation formulation of the transport equation is used to relate (1) the difference between the measured and predicted detector readings in the target and reference, respectively, to (2) a difference between the unknown and known internal properties of the target and reference, respectively. This relationship is solved for the unknown scattering and absorption properties of the target. The final distributions of internal properties are then displayed or printed as an image.

Imaging systems based on scattering techniques, such as optical tomography systems, provide a means with which to examine and image the internal properties of scattering media, such as the absorption and diffusion or scattering coefficients. However, a problem with the known systems and methods-is that of inter-coefficient crosstalk. Inter-coefficient or parameter crosstalk refers to instances where, for example, localized variations in absorption appear, in the recovered image, as localized variations in scattering, or vice versa. For instance, the vasculature can be imaged because the absorption coefficient of the blood contrasts with the absorption coefficient of the surrounding tissue. Similar variations in the scattering or diffusion coefficient may be present through the tissue as a result of glucose levels or nerve activation. The problem of crosstalk relates to determining whether a change in a detector reading on the surface of the target is the result of a change in the absorption coefficient or the scattering coefficient. The problem is that in the attempt to image the vasculature by examining absorption coefficients, the image may be distorted by variations in the scattering or diffusion coefficient that have leaked into the absorption coefficient.

For the foregoing reasons, there is a need for a method of minimizing inter-coefficient crosstalk to more accurately and reliably resolve the scattering and absorption coefficients in image reconstruction.

SUMMARY OF THE INVENTION

The present invention satisfies this need by providing a method and system for image reconstruction and data collection that minimizes inter-coefficient crosstalk.

One object of the invention is to minimize crosstalk by (1) generating a system of linear perturbation equations, (2) scaling the weight matrix or matrices of the linear perturbation equations, and (3) constraining the solution of the linear equations by either (a) applying one of a positive or a negative constraint where the direction of the perturbation is known, or (b) solving the system of linear perturbation equations twice, first with a positivity constraint and second with a negativity constraint where the direction of the perturbation is unknown. The linear perturbation equations solved with a positivity constraint are only permitted to have a positive perturbation in the solution at each iteration, any negative solutions are overridden; a negative constraint only permits negative solutions. The positively and negatively constrained solutions may then be summed to produce a solution with minimal crosstalk.

A further aspect of the invention is to minimize crosstalk by using relative detector values in place of absolute values in the linear perturbation equations.

Using the inventive techniques, the crosstalk between the internal properties such as the absorption and scattering coefficient can be minimized and the coefficients more clearly resolved so that perturbations in one coefficient do not effect the other.

The foregoing specific objects and advantages of the invention are illustrative of those which can be achieved by the present invention and are not intended to be exhaustive or limiting of the possible advantages that can be realized. Thus, the objects and advantages of this invention will be apparent from the description herein or can be learned from practicing the invention, both as embodied herein or as modified in view of any variations which may be apparent to those skilled in the art. Accordingly, the present invention resides in the novel parts, constructions, arrangements, combinations and improvements herein shown and described.

BRIEF DESCRIPTION OF THE FIGURES

The patent file contains at least one drawing executed in color. Copies of this patent with color drawing(s) will be provided by the Office upon request and payment of the necessary fee.

For a better understanding of the invention, together with the various features and advantages thereof, reference should be made to the following detailed description of the preferred embodiments and to the accompanying drawings wherein.

DETAILED DESCRIPTION OF THE INVENTION

1. Introduction

The ability to accurately define the absorption and scattering properties of tissue could significantly add to the diagnostic sensitivity and specificity of optical measurements. In the case of imaging studies, a common problem is inter-parameter crosstalk [1]. This refers to instances where, for example, localized variations in absorption also appear, in the recovered image, as localized variations in scattering, or vice versa. This issue can arise from fundamental reasons related to the intrinsic information content of a data set, as well as from reasons related to the numerical methods used to reconstruct coefficient maps. In the case of DC measurement data, Arridge and Lionheart [2] have claimed to have rigorously proven that there is an underlying non-uniqueness in the inverse problem (i.e., the solution to the system of linear perturbation equations), and have strongly emphasized that total intensity measurements from surface detectors alone are insufficient to distinguish effects of absorption from effects of scattering.

The present invention describes a new algorithm (i.e., the normalized-constraint algorithm) for imaging the absorption and scattering coefficients of a scattering medium while minimizing crosstalk and demonstrates the ability to separate local perturbations in absorption and scattering, under a wide range of conditions. Contrary to previous assertions [2,3], the method of the present invention demonstrates that spatial variations in the absorption and scattering properties of highly scattering media can be resolved with minimal crosstalk.

For illustration purposes, the present system and method is described in further detail below with respect to an optical tomography system used to generate cross-section images or slices of a target scattering medium. However, it will be appreciated by those skilled in the art that the methodology of the present invention is applicable in image reconstruction from measured data based on any energy source (e.g., electromagnetic, acoustic, etc.), any scattering medium (e.g., body tissues, oceans, foggy atmospheres, geological strata, and various materials, etc.), any source condition (e.g., time-independent, time-harmonic, time-resolved) and any physical imaging domain (e.g., cross-sectional, volumetric). Its applicability is dependent only on the presence of the phenomenology described herein (i.e., radiative transfer being the principal mechanism of energy transport), which is expected in all cases where scattering occurs. Accordingly, this methodology can be extended to allow for new imaging approaches in a broad range of applications, including nondestructive testing, geophysical imaging, medical imaging, and surveillance technologies.

2. Exemplary Measuring System

Figure 1:
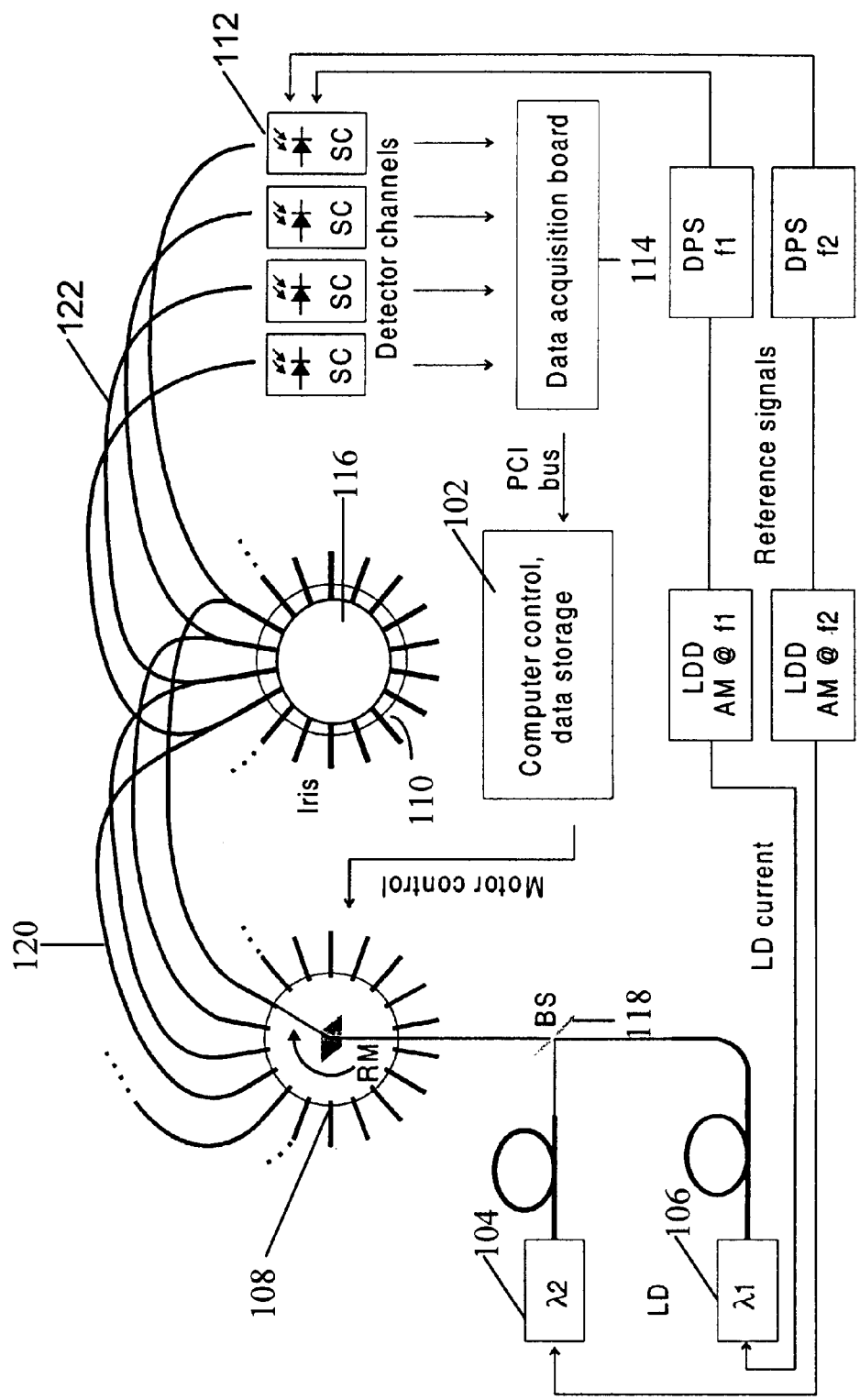
FIG. 1 is a schematic of an exemplary measurement and imaging system.

There are many known imaging systems for collecting the measured data used in image reconstruction in scattering media. A schematic illustration of an exemplary optical tomography system is shown in FIG. 1. This system includes a computer 102, energy source 104, a fiber switcher 108, an imaging head 110, detectors 112, a data acquisition board 114, source fibers 120 and detector fibers 122.

The energy sources 104 and 106 provides optical energy, directed through a beam splitter 118, to the fiber switcher 108 and then to each of the plurality of source fibers 120 one at a time in series. The source fibers 120 are arranged around an imaging head 110 so that the energy is directed into the target medium 116 at a plurality of source locations around the target.

The energy leaves the source fiber 120 at the imaging head 110 and enters the target medium 116 centered in the imaging head 110. The energy is scattered as it propagates through the target medium, emerging from the target medium at a plurality of locations. The emerging energy is collected by the detector fibers 122 arranged around the imaging head 110. The detected energy then travels through the detector fibers 122 to detectors 112 having energy measuring devices that generate a signal corresponding to the measurement. The data acquisition board 114 receives the measurement signal for delivery to the computer 102.

This process is repeated for each source position so that a vector of measures are obtained for all of the detectors and source locations. This vector of measured data is the vector u referred to below. The vector of data u is stored by the computer 102 for use in image reconstruction and other analysis discussed below. The computer 102 or other suitable processing device or hardware is used to process the collected data and reconstruct the image as described in detail by the methods below.

2. Methods

The method of the present invention is a modification of known techniques using perturbation methods such as those disclosed in the Barbour, PCT Publication No. WO 01/20546 A2, entitled "Imaging of a Scattering Medium Using Relative Detector Value" (the "Barbour '546 publication") and the Barbour, PCT Publication No. WO 01/20306 A1, entitled "System and Method for Tomographic Imaging of Dynamic Properties of a Scattering Medium" (the "Barbour '306 publication").

The normalized-constraint algorithm for minimizing inter-coefficient crosstalk employs a three-step process.

First, relative detector readings or measurements are used instead of absolute values, based on a previously developed inverse formulation called the normalized difference method [4]. This is done in recognition of the practical limits imposed on obtaining reliable absolute measurement data from arbitrary structures such as tissue. This is also done in recognition of the fact that perturbation methods, in general, tend to yield grossly incorrect solutions if the reference medium used to generate the initial guess differs sufficiently from the actual target background properties. As described in recent reports [4–6], selection of insufficiently accurate reference media can severely alter the information content of the data vector. Once corrupted, the recovery of images relatively free of artifact can be very difficult or impossible, even with use of full Newton updates.

The second step scales the weight matrix, by normalizing the column vectors to their respective mean values, to obtain a transformed formulation. This makes the weight matrix in the new system equation more uniform and less ill-conditioned, and also serves to suppress numerical errors and accelerate convergence [7,8].

The third step employs a constrained CGD method for solving the resulting system equation, where positivity or negativity constraints are imposed on iteratively computed estimates of the medium's absorption coefficient and diffusion or scattering coefficients. Ordinarily, this option is not applicable to the general case wherein the sign of the perturbation is unknown. As described below, by adopting a two-step process where solutions are obtained for both signs of the constraints and then summed, satisfactory solutions can be obtained.

While the first relative detector reading step in combination with the weight matrix scaling and constraint steps serve to produce the most reliable and accurate results, crosstalk may also be reduced in absolute detector readings by applying the scaling and constraint steps. The details of these steps and their place in the reconstruction process are discussed further below.

2.1 Forward Model

As discussed above, typical reconstruction techniques are based on perturbation methods that essentially relate the difference between predicted detector measurements from a reference medium and detector measures form the target, to solve for the difference between unknown properties of the target and known properties of the reference. Accordingly, one of the first steps in reconstruction is to select a reference medium and predict the detector readings by modeling or physical measure. Modeling the energy propagation in the scattering medium is done using the transport equation or its approximation, the diffusion equation. The equations describe the propagation of photons through a scattering medium. For a domain having a boundary $\partial \Lambda$, this is represented by the expression:

$$\nabla[D(r)\nabla u(r)] - \mu_a(r)u(r) = -\delta(r-r_s), \quad r \in \Lambda, \qquad (1)$$

where $u(r)$ is the photon intensity at position r, $r_s$ is the position of a DC point source, and $D(r)$ and $\mu_a(r)$ are the position-dependent diffusion and absorption coefficients, respectively. Here the diffusion coefficient is defined as $D(r) = 1/\{3[\mu_a(r) + \mu_s(r)]\}$, where $\mu_s(r)$ is the reduced scattering coefficient. Using this equation the energy emerging from the reference medium at each detector location for each source location is predicted. The transport or diffusion equations are also the basis for formulating the perturbation or inverse formulation used in reconstruction.

2.2 The Inverse Formulation

As discussed above, reconstruction of a cross-sectional image of the absorption and/or scattering properties of the target medium is based on the solution of a perturbation or inverse formulation of the radiation transport or diffusion equation. The perturbation method assumes that the composition of the unknown target medium deviates only by a small amount from a known reference medium. This reduces a highly non-linear problem to one that is linear with respect to the difference in absorption and scattering properties between the target medium under investigation and the reference medium. The resulting optical inverse or perturbation formulation is based on the normalized difference method [3–6] and has the following form:

$$W_r^{(\mu_a)} \cdot \delta\mu_a + W_r^{(D)} \cdot \delta D = \delta u_r, \qquad (2)$$

where $\delta\mu_a$ and $\delta D$ are the vectors of cross-sectional differences between the optical properties (absorption and diffusion coefficients, respectively) of a target (measured) medium and of a reference (computed or measured) medium used to generate the initial guess; $W_r^{(\mu_a)}$ and $W_r^{(D)}$ are the weight matrices describing the influence that localized perturbations in the absorption and diffusion coefficients, respectively, of the selected reference medium have on the surface detectors; and $\delta u_r$ represents a normalized difference between two sets of detector readings, which is defined by the equation:

$$(\delta u_r)_i = \left(\frac{(u_1)_i - (u_2)_i}{(u_2)_i}\right)(u_r)_i, \quad i = 1, 2, \ldots, M. \qquad (3)$$

Here, $u_r$ is the computed detector readings corresponding to the selected reference medium, $u_2$ and $u_1$ represent two sets of measured data (e.g., background vs. target, time-averaged mean vs. a specific time point, etc.) and M is the number of source-detector pairs in the set of measurements.

2.3 Weight Matrix Scaling

The effect of scaling the weight matrix is to make it more uniform, which can often serve to improve its conditioning. A scaling method that serves to improve the conditioning of the absorption weight matrix is described in by Chang et.al. [7]. This method is extended in the present invention to the case in which absorption and scattering or diffusion coefficients are recovered simultaneously. A scaling approach that scales each column of war and $W_r^{(\mu_a)}$ and $W_r^{(D)}$ to the average value of the column vector is used. However, it should be understood that any of the known scaling approaches could be adopted. The form of the resulting new weight matrices is:

$$W_r^{\%(k)} = W_r^{(k)} \cdot R^{(k)}, \quad (4)$$

where, k can be $\mu_a$ or D, and $R^{(k)}$ is the normalizing matrix whose entries are:

$$(R^{(k)})_{ij} = \begin{cases} \dfrac{1}{\frac{1}{M}\sum_{m=1}^{M}(W_r^{(k)})_{mj}} & j = 1, \\ 0 & j \neq 1, \end{cases} \quad i, j = 1, 2, \ldots, N, \quad (5)$$

in which N is the number of elements used in discretizing the domain $\Lambda$. The resulting system equation is:

$$\tilde{W}_r^{(\mu_a)} \cdot \delta\mu_a + \tilde{W}_r^{(D)} \cdot \delta\tilde{D} = \delta u_r, \quad (6)$$

where $\delta\mu^\%_a = [R^{(\mu_a)}]^{-1} \cdot \delta\mu_a$ and $\delta D^\% = [R^{(D)}]^{-1} \cdot \delta D$.

2.4 Solutions of the System of Perturbation Equations

The CGD method is used to solve the system of equations and demonstrates the invention, however, any method of solving simultaneous equations, in which the solution can be constrained, may be used.

For most measurement geometries the weight matrix $W_r^\%$ is not symmetric positive definite, and the usual practice is to seek a least-squares solution of the system of linear equations shown in Eq. (6). This solution is found by minimizing the mean-squared error E, represented as:

$$E = \tfrac{1}{2}(W_r^\% \cdot \delta x^\% - \delta u_r)^T (W_r^\% \cdot \delta x^\% - \delta u_r) = \tfrac{1}{2}\delta x^{\%T} \cdot A \cdot \delta x^\% - b^T \cdot \delta x^\% + \tfrac{1}{2}\delta u_r^T \cdot \delta u_r, \quad (7)$$

where $\delta x^\% = [\delta\mu_a^{\%T} \delta D^{\%T}]$, $W_r^\% = [W_r^{\%(\mu_a)} W_r^{\%(D)}]$, $A = W_r^{\%T} \cdot W_r^\%$ and $b = W_r^{\%T} \cdot \delta u_r$.

Formally, the least-squares solution is obtained by setting the derivative of E to 0, i.e., $$g(\delta x\%) = \frac{\partial E}{\partial(\delta x\%)} = A \cdot \delta x\% - b = 0. \quad (8)$$

When the CGD method is applied, instead of explicitly solving Eq. (8), the following iterative formulation is employed for computing $\delta x$:

$$\delta x^{\%(n)} = \delta x^{\%(n-1)} - \alpha^{(n)} d^{(n)}. \quad (9)$$

The iterative procedure is:

1) Based on an initial estimate of $\delta x^{\%(0)}$, compute $$g^{(0)} = A \cdot \delta x^{\%(0)} - b; \quad d^{(1)} = -g^{(0)}; \quad \beta^{(1)} = 0;$$

2) For the $n^{th}$ iteration, compute $$\alpha^{(n)} = \frac{\|g^{(n-1)}\|^2}{\|W_r^\% \cdot d^{(n)}\|^2},$$

where:

$$g^{(n-1)} = A \cdot \delta x^{\%(n-1)} - b (= g^{(n-2)} - \alpha^{(n-1)} A \cdot d^{(n-1)}), \text{ and}$$

$$d^{(n)} = -g^{(n-1)} + \beta^{(n)} d^{(n-1)}, \quad \beta^{(n)} = \frac{\|g^{(n-1)}\|^2}{\|g^{(n-2)}\|^2}.$$

The present invention minimizes crosstalk by constraining the solutions. Where the direction of the perturbation is known, the solution is constraint negatively or positively to correspond to a negative or positive perturbation, respectively. Where the direction of the perturbation is unknown, a two-step process is adopted; imposing one set of constraints (i.e., positivity on one coefficient and negativity on the other, or positivity or negativity on both coefficients), then reversing these. It will be understood by those skilled in the art that a range constraint may also be imposed on the solution. The sum of the two partial solutions thus obtained results in the vectors $\delta\mu_a^{(n)}$ and $\delta D^\%$. In the examples discussed below, positive or negative constraints are separately imposed on the reconstruction results $\delta\mu_a^{(n)}$ and $\delta D^{\%(n)}$ after each iteration. In some instances, prior knowledge of the direction of the perturbation is assumed and the appropriate constraint applied.

After the intermediate solutions ($\delta\mu_a^{(n)}$ and $\delta D$) are computed, they are rescaled to get the final results, via the formulas:

$$\delta\mu_a = R^{(\mu_a)} \cdot \delta\mu_a^\%; \quad (10)$$

$$\delta D = R^{(D)} \cdot \delta D^\%.$$

For all reconstruction results discussed below, solutions were limited to a first-order computation involving at most 1000 CGD iterations. The finite-element grid used comprised 1296 elements. The optical properties of the reference medium used for the initial guess were $\mu_a$32 0.04 cm$^{-1}$ and $\mu_s$=10 cm$^{-1}$ (D≈0.0332 cm) for the numerical studies, and $\mu_a$=0.02 cm$^{-1}$ and $\mu_s$=10 cm$^{-1}$ (D≈0.0333 cm) for the experimental studies.

While implementation of the present invention has been detailed using the conjugate gradient descent (CGD) method to solve the system of equations, it will be apparent to one skilled in the art that other methods such as simultaneous algebraic reconstruction (SART), projection onto convex sets (POCS) or the like may similarly be used in practicing the invention. Additionally, while using the first two steps of the methodology discussed above to enhance the accuracy and reliability of the results, it will be understood to those skilled in the art that the present invention may be practiced without these two steps. That is for example, absolute detector values may be used instead of relative detector values, or the scaling step may be omitted.

3. Simulation Results

Figure 2:
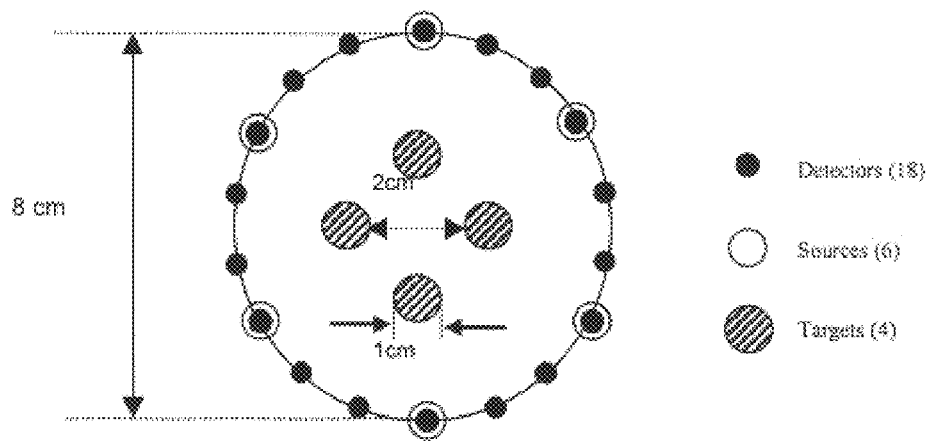
FIG. 2 is a cross-sectional illustration of a target medium and the geometrical arrangement of sources, detectors and embedded objects.

FIG. 2 shows a sketch of the target medium considered for the simulation studies. As many as four objects, symmetrically positioned and having the dimensions and locations shown, were included. Each tomographic simulation considered 6 sources and 18 detectors, providing 108 source-detector pairs. The detector responses for the target medium and those corresponding to a selected reference medium having the same external geometry, size and source-detector configuration were computed. Simulated data from these calculations were subsequently analyzed using the methods described above.

Figure 3:
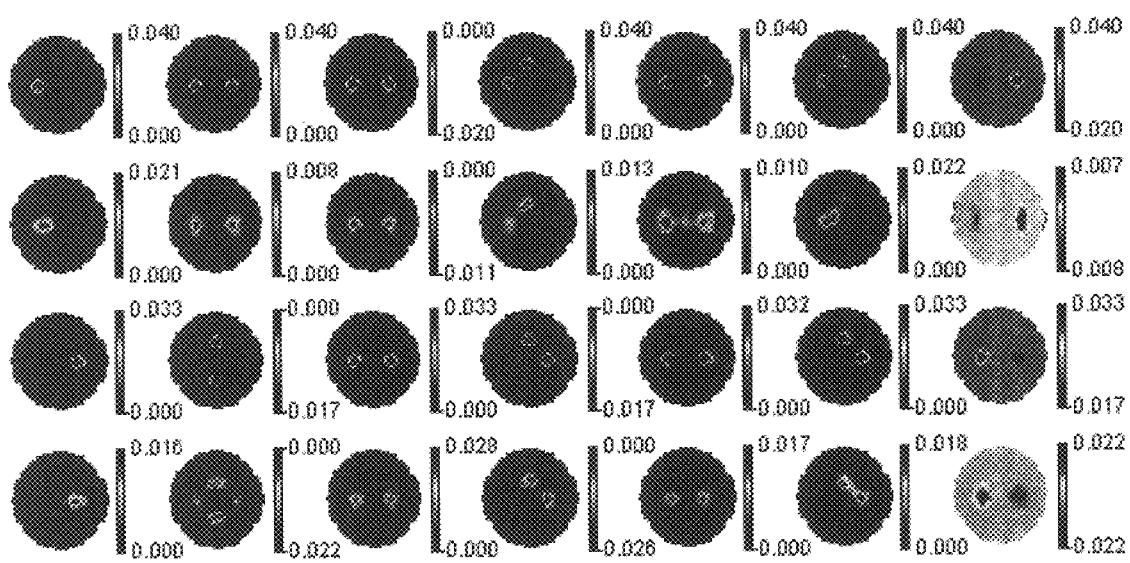
FIG. 3 is a series of original and reconstructed images of the cross-sectional properties of a target medium shown in FIG. 2.

FIG. 3 shows the original and reconstructed profiles for the target medium considered. Rows one and three are the original profiles for $\delta\mu_a$ and $\delta D$, respectively; rows two and four are the corresponding reconstructed profiles. The scale indicates the magnitude and sign of the perturbation. Proceeding from left to right, in the first column two objects are present. In the left-hand inclusion, only the $\mu_a$ value is increased ($\delta\mu_a$=0.04 cm$^{-1}$) relative to the background; in the right-hand inclusion, only the D value is increased ($\delta D \approx 0.033$ cm). In the second column, four objects are considered. Here only one of the two coefficients is perturbed in any given object. For the left- and right-hand inclusions, the $\mu_a$ value is increased ($\delta\mu_a$=0.04 cm$^{-1}$); for the top and bottom inclusions, the D value is decreased ($\delta D \approx -0.017$ cm). In columns 3–7 the more general case where perturbations in both $\mu_a$ and D can occur simultaneously in any object are considered. In column three, two inclusions are present, and the $\mu_a$ and D values of both are decreased ($\delta\mu_a$=−0.02 cm$^{-1}$) and increased ($\delta D \approx 0.033$ cm), respectively. In column four, three objects are present. In the left-hand and top inclusions the $\mu_a$ value is increased ($\delta\mu_a$= 0.04 cm$^{-1}$), while the D value is decreased in the right-hand and top inclusions ($\delta D \approx -0.017$ cm). Thus, it is only the top inclusion that has perturbations in both coefficients, while the left- and right-hand inclusions have perturbations in only $\mu_a$ and only D, respectively. In the case of columns five and six, the locations of the objects and the pattern of their coefficient value perturbations are the same as those in columns three and four, respectively. What differs is the direction of the perturbation for one of the coefficients. For column five, the $\mu_a$ of the inclusions was increased by 0.04 cm$^{-1}$ relative to the background, while $\delta D$ is the same as that in column three. For column six, only the D value for the top and right-hand inclusions differs from that in column four. Here, the $\delta D$ value was ~0.033 cm, while the $\mu_a$ value for the right-hand and top inclusions remains unchanged.

It is worth noting that these latter two cases are similar to the more difficult examples explored by Arridge and Lionheart [2], in which the influence of an increase or decrease in an object's absorption coefficient on surface measurements can be offset by a decrease or increase, respectively, in the value of its scattering coefficient (i.e., increase or decrease in D). These are conditions where evidence for solution nonuniqueness using intensity-only data was presented. Finally, in column seven, the $\delta_a$ and D values for the inclusions were decreased and increased, respectively, in the left-hand object ($\delta\mu_a$=−0.02 cm$^{-1}$, $\delta D \approx 0.033$ cm), while the opposite trend occurs in the right-hand object ($\delta\mu_a$=0.04 cm$^{-1}$, $\delta D \approx -0.017$ cm).

Inspection of the reconstructed profiles shows that in each case the perturbations in the absorption and diffusion coefficients are effectively isolated, whether or not they are co-located. In the first six cases this was accomplished by assuming prior knowledge of the sign of the perturbation and applying the appropriate constraint as described in Section 2. In practice, this could correspond to situations where the influence of a particular manipulation of tissue (e.g., inflation of a pressure cuff) would impose an expected response (e.g., venous congestion and hence an increase in absorption by hemoglobin). Note that in columns two and four, a small degree of image contrast is seen in the D image in the locations where only perturbations in $\mu_a$ occur. This is not completely attributable to crosstalk, as a positive perturbation in $\mu_a$ will be expected to produce a small negative perturbation in D[9], which is observed. A corresponding result is not seen in columns one and six because of the positivity constraint applied to the D reconstruction.

The more general case, shown in column seven, is that in which the perturbation in either coefficient could be positive or negative. To capture this information a two-step process is applied. First, we imposed a positivity constraint on one coefficient and a negativity constraint on the other. Second, the directions of these constraints are reversed and the two solutions are summed together. The resulting images clearly show that parameter isolation is achieved with a high degree of fidelity and spatial accuracy. In fact, the spatial localization of the reconstruction is in most cases excellent. This finding is even more notable when it is considered that the results presented are limited to a first-order solution. As commented below, this appears to originate from the considerably different structure of the Jacobian-operator that results from matrix scaling.

4. Experimental Results

To validate the normalized-constraint method, a series of laboratory studies were conducted on vessels containing one or more objects whose optical properties differ from a homogeneous background primarily in either its scattering or scattering and absorption coefficients. In addition to acting as optical perturbations, dynamic behavior was introduced by translating the objects along circular arcs as indicated (see FIG. 4), while all the time acquiring fast tomographic data sets using the DC imager described in the Barbour '306 publication and Schmitz et. al. [10].

Figure 4:
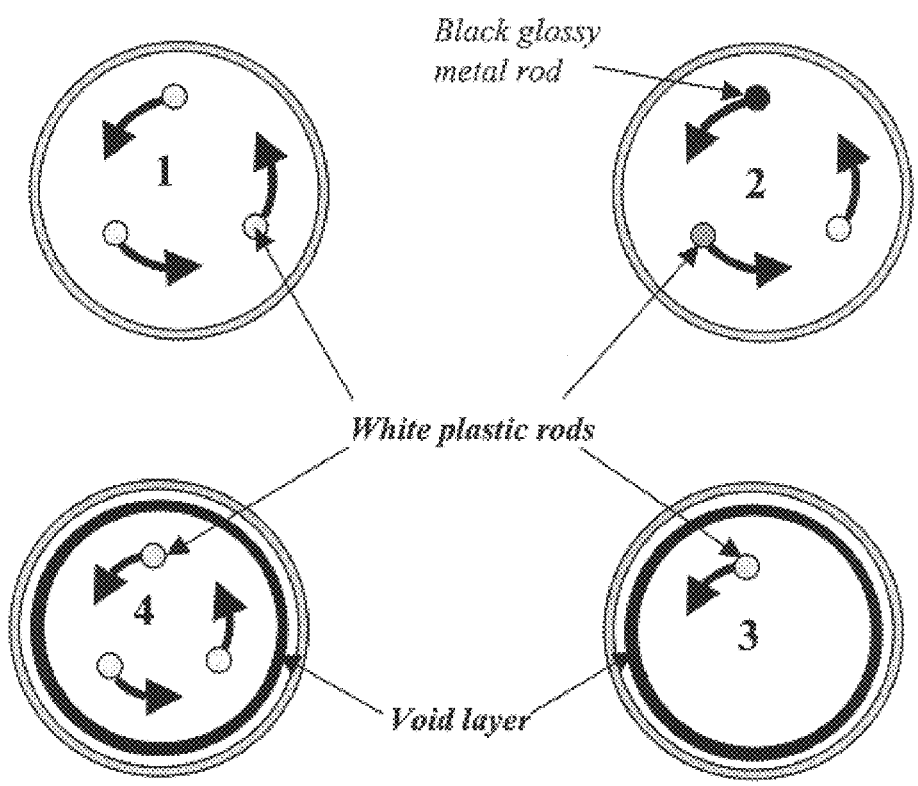
FIG. 4 are illustrations of a series of target media.

Sketches of the target media explored are shown in FIG. 4. In case one, three rods (6 mm dia.) composed of white Delrin were introduced into a hollow cylindrical vessel, also composed of white Delrin, having an outer diameter of 7.6 cm and filled with 1% (v/v) Intralipid. It has been reported that the optical properties of white Delrin are $\mu_a \approx 0.02$ cm$^{-1}$, $\mu_s \approx 12$ cm$^{-1}$[11], while those of 1% Intralipid are $\mu_a \approx 0.02$ cm$^{-1}$, $\mu_s \approx 10$ cm$^{-1}$[12]. Thus, it is only the scattering coefficient of the rods that is increased (decreased D) relative to the background. The detected light intensity was increased on the same side of the vessel as the source, and decreased on the side opposite the source, in the presence of the rods, a finding consistent with the reported coefficient values.

In case two, a similar experiment was performed, except that one of the Delrin rods was replaced by a black glossy metal rod having a similar diameter. This substitution was treated as introducing perturbations in both the absorption and scattering coefficients. In cases three and four we performed similar studies, except here the complexity of the medium was increased via the introduction of a 3-mm-thick clear plastic layer that served as an optical void. These cases were intended to determine whether the methods could correctly isolate optical perturbations (and dynamic behavior) under conditions where the assumptions of the diffusion equation are strongly violated. Data acquisition involved 16 equally spaced source positions with 16 co-located detectors (256 source-detector pairs). The illumination wavelength was 785 nm (10 mW), and full tomographic scans were acquired at 3 Hz for approximately 25 seconds (75 scans).

Figure 5:
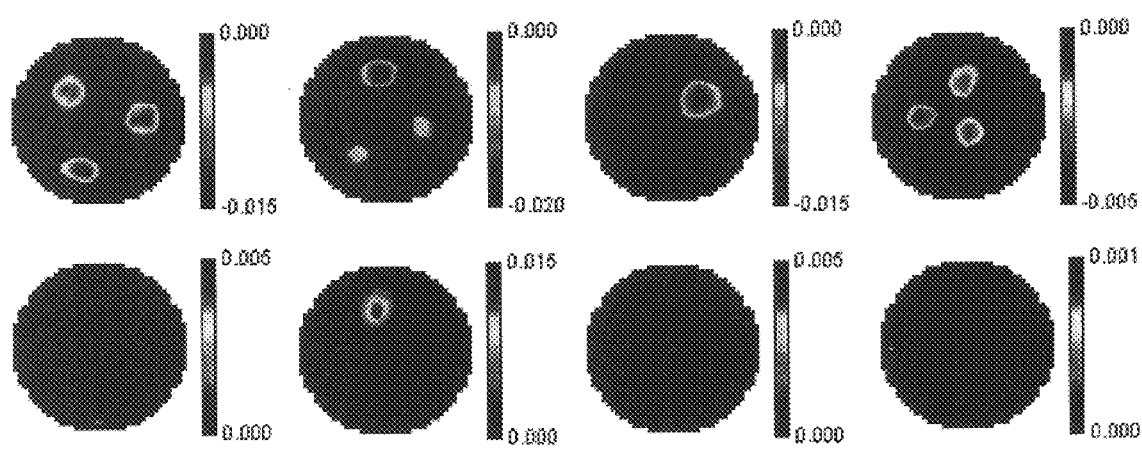
FIG. 5 is a series of reconstructed images of the cross-sectional diffusion and absorption profiles for the target of FIG. 4.

FIG. 5 shows typical reconstructed profiles of the diffusion (top row) and absorption (bottom row) coefficients for the four cases obtained using the two-step constraint protocol. Column one (left side) shows the reconstructed profiles corresponding to case one. Inspection shows nearly complete separation of the absorption and diffusion coefficients. The absorption image reveals that the artifact is restricted to the region near the boundary, while the interior is almost completely featureless. The reconstructed diffusion image shows, with high contrast, the correct locations of the inclusions. Quantitative comparison of the image data reveals that the amplitudes of the computed $\mu_a$ perturbations are quite small in absolute terms and also small compared to the magnitude of the computed perturbation in D, revealing minimal crosstalk.

Another feature observed, particularly in solutions obtained using Eq. (2), is that the recovered $\delta\mu_a$ and $\delta D$ values scale with the selected reference medium used to compute $u_r$ and $W_r$, their ratio does not (results not shown). That is, the relative magnitude of crosstalk between the absorption and diffusion images is essentially independent of the optical coefficient values chosen for the reference medium used as the initial guess.

Column two shows that results of similar quality to those in case one are obtained when both coefficients are perturbed. Note that the inclusion contrast for this case is qualitatively similar to that associated with column four of FIG. 3, where one of the three inclusions has contrast in both coefficients. The presence of the plastic rods is revealed only in the reconstructed diffusion images, whereas the glossy black metal rod appears in both the recovered diffusion and absorption images. As in case one, nearly complete isolation of absorption and diffusion coefficients is obtained for the included plastic rods, with only minimal distortion of object shape and location. For cases one and two, object contrast and resolution actually were improved when the $\mu_s'$ value used for the initial guess was lowered from 10 $cm^{-1}$ to 3 $cm^{-1}$.

Data in columns three and four show results obtained in the presence of a circular optical void (cases three and four). This geometry was considered as a crude representation of the layered structure that occurs in the head. Here, the void is meant to represent the layer of clear cerebrospinal fluid that lies in the subarachnoid space. This case was considered because it has been reported by Dehghani et al. that reconstruction methods based on the diffusion approximation perform poorly under conditions similar to those examined here [13]. In the case of a single inclusion (white plastic rod, column three), the presence of the optical void does not prevent nearly complete separation of the coefficient profiles. Data in column four shows that qualitatively similar results are obtained using three plastic rods, in terms of minimizing crosstalk, although increased artifacts are present. Note that the images of the rods in this case are more centrally located than those in case one and correspond closely to their actual spacing. These findings show that, using the methods described here, the difficulties that Dehghani et al. reported using diffusion-based imaging codes [13] are not present. Finally, the above analyses were repeated for both simulated and experimental data using a wide range of reference media as the initial guess [4–6]. In all cases, the image quality obtained did not differ substantially from that presented here.

Dependence of Image Quality on Use of Constraints and Matrix Scaling Methods

Figure 6:
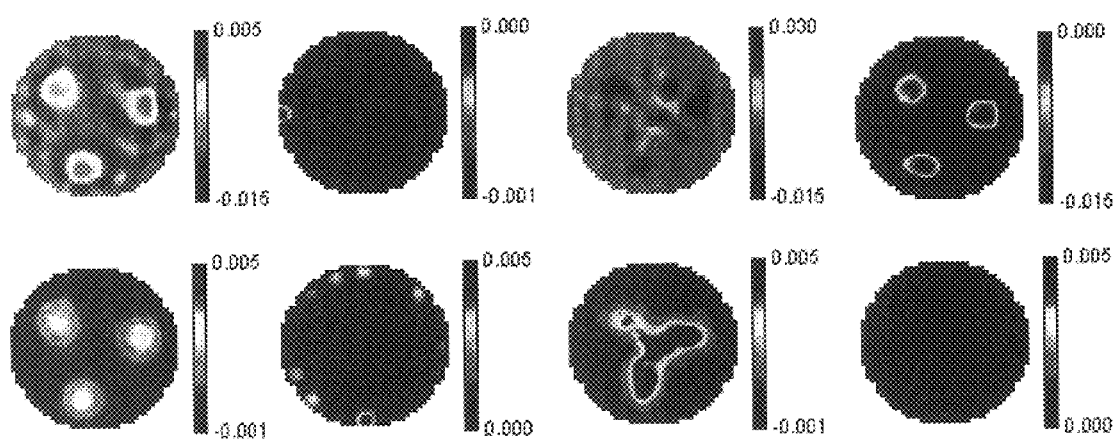
FIG. 6 is a comparison of reconstructed images of the cross-sectional diffusion and absorption profiles using various CGD methods.

Results shown thus far have corresponded to findings obtained when the CGD method was extended by introducing two modifications. The first is to implement a range constraint; the second is to solve Eq. (6) using a scaled weight matrix. It is instructive to examine the influence that the additional operations separately have on image quality and parameter isolation. Results in FIG. 6 show snapshots of dynamic behavior of the recovered coefficients when CGD only (column one), CGD with range constraints (column two), CGD with matrix scaling (column three) and CGD with range constraints and matrix scaling (column four) methods were used to reconstruct the images. The top row corresponds to the reconstructed $\mu_a$, the bottom row to reconstructed D. The experimental data analyzed are the same as those that produced the results shown in column one of FIG. 5 (i.e., three plastic rods). The input data vectors are quantities normalized to the temporal mean value for each respective source-detector channel. Results in column one (CGD only) show that the three-rod structure is clearly resolved in the $\mu_a$ map. While the spatial locations and resolution of the inclusions are notable, the result obtained is almost completely attributable to inter-parameter crosstalk. Inspection of the D map in column one shows that the three-rod structure is also recovered with the correct sign of the perturbation ($\delta D<0$), but the image quality is impaired by artifact. Results in column two show that introduction of a range constraint (positivity on $\mu_a$, negativity on D) produces a result dominated by artifact on the boundary, with significant loss of internal structure. Results in column three show that use of a scaled weight matrix alone produces a rather unsatisfactory answer. The D image map is heavily dominated by artifact, and crosstalk is evident in the $\mu_a$ map. Results in column four are a reproduction of those shown in column one of FIG. 5, and reveal excellent parameter isolation and spatial resolution. Accordingly, it is only in combination that the desired result is obtained.

Influence of Scaling on the Structure of the Weight Matrix

Figure 7:
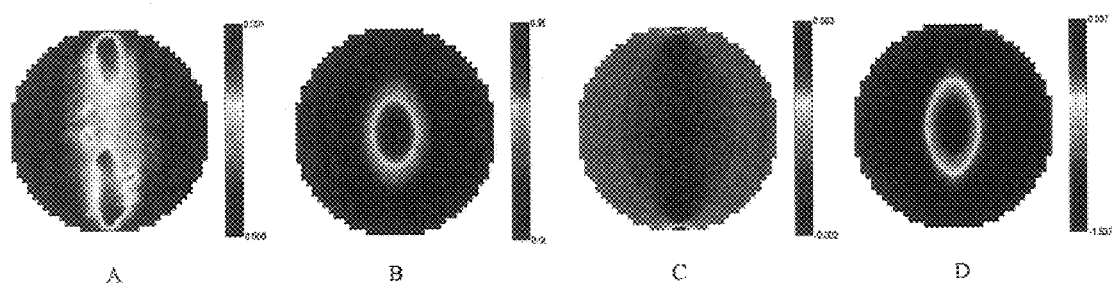
FIG. 7 is a series of cross-sectional images of the weight functions and diffusion coefficients corresponding to the source detector pairs.

It is apparent that the combined methods provide for a satisfactory answer. In an effort to further understand the influence of matrix scaling, we have compared the structure of scaled and unscaled weight matrices. These are shown as snapshots in FIG. 7, for both optical coefficients, as functions of different source-detector configurations. Panels A and C correspond to unscaled weight matrices for $\mu_a$ and D, respectively. Panels B and D are the corresponding scaled weight matrices. Inspection of the unscaled matrices reveals the well-known "banana" structure, with the region of greatest weight occurring in the vicinity of the source and detector. The structure of the scaled matrices, on the other hand, is notably different. Here the region of highest normalized weight occurs in the interior. This demonstrates that matrix scaling effectively redistributes regions of importance. The net effect for all source-detector pairs is to produce a more uniform weighting of the contributions of the various regions of the target, rather than the bias towards the surface for unscaled weight matrices.

5. Conclusions

The present invention addresses the problem of interparameter crosstalk involving simultaneous reconstruction of images of spatial distributions of the absorption and diffusion coefficients of highly scattering media. By imposing range constraints and scaling the weight matrix, perturbations in one coefficient can be effectively isolated from those in the other.

This capability of the present invention, verified by experiment, is in striking contrast to the findings that might be expected on the basis of theoretical studies by Arridge and Lionheart [2], who demonstrated an underlying nonuniqueness between the optical properties of a scattering medium and the surface intensities. Specifically, it was shown that a "null space" state can exist, in which the effects of pairs of absorption and scattering coefficient distributions on the surface intensity effectively cancel each other. The inference drawn in the litrature [2,3] and by reviewers of recent work who point to it is that, given a set of detector responses, essentially any spatial map can be derived because of the "null space" phenomenon. From this it would seem to logically follow that DC imaging methods should not be capable of providing useful information. As shown by results presented here and in several recent reports [10, 14–16, 17,18], this is not the collective experience.

Whereas parameter isolation is best achieved when the direction of the constraint is known, as noted, use of an inappropriate constraint can lead to a grossly incorrect solution. In instances where the two-step constraint is applied, it is the case that only half of the applied constraints can be correct. In these circumstances, the two-step process can lead to increased artifact levels in the extreme boundary (cf. column seven, FIG. 3). These artifacts are seen almost exclusively in the region of the extrapolated boundary. As this extends beyond the physical boundary, this region has been excluded from the image results shown for the experimental studies.

Influence of Nonuniqueness on DC Imaging Studies.

Another point which deserves emphasis is the practical utility of methods for characterizing the optical properties of highly scattering media. For the current report the diffusion approximation to the radiation transport equation was used when computing the weight matrices and reference detector readings that enter the system equation (Eq. (6)). It is widely appreciated that this formulation is not well suited for predicting light distributions in media containing voids [20]. As noted above, however, by using this approach we are nevertheless fully capable of separating absorption from scattering, defining object location and observing dynamic behavior, even in the presence of a 3-mm-thick clear circular layer. These findings stand in marked contrast to a recent report by Dehghani et al. [13] who performed a largely similar experiment involving numerical simulations on a static medium. They found that in cases where the thickness of the circular void approaches 1 mm, resolution of internal structure is completely lost. Common to both studies is a pronounced mismatch between the conditions that propagating photons experience in the medium and those that are assumed to exist in the model used for image recovery. In the computations presented in Ref. 13, this was modeled by considering a two-dimensional medium containing a non-scattering ring wherein the inverse problem was solved using the diffusion approximation, while the forward problem was solved using the transport equation. The apparent discrepancy can be attributed mainly to the different types of detector data considered. The above cases examine a differential measure, while Dehghani et al. do not. This consideration is consistent with a recent report wherein we demonstrated that the quality of information derived from examination of light-field distributions can vary greatly depending on the specifics of the how the data vectors are treated [4]. It would seem that the practical limits of inferring useful information from highly scattering media are not as restrictive as some have perceived.

Although illustrative embodiments have been described herein in detail, those skilled in the art will appreciate that variations may be made without departing from the spirit and scope of this invention. Moreover, unless otherwise specifically stated the terms and expressions used herein are terms of description and not terms of limitation, and are not intended to exclude any equivalents of the system and methods set forth in the following claims.

Appendix

1. T. O. McBride, B. W. Pogue, U. L. Österberg, and K. D. Paulsen, "Separation of absorption and scattering heterogeneities in NIR tomographic imaging of tissue," in Biomedical Topical Meetings, OSA Technical Digest (Optical Society of America, Washington, D.C., 2000), pp. 339–341.

2. S. R. Arridge and W. R. B. Lionheart, "Nonuniqueness in diffusion-based optical tomography," Opt. Lett. 23, 882–884 (1998).

3. J. C. Hebden, S. R. Arridge and M. Schweiger, "Investigation of alterative data types for time-resolved optical tomography," Trends in Optics and Photonics vol. 21, Advances in Optical Imaging and Photon Migration, James G. Fujimoto and Michael S. Patterson, eds. (Optical Society of America, Washington, D.C. 1998), pp 162–167.

4. Y. Pei, H. L. Graber and R L. Barbour, "Influence of systematic errors in reference states on image quality and on stability of derived information for DC optical imaging," Appl. Opt., 2001, in press.

5. Y. Pei, Optical Tomographic Imaging Using the Finite Element Method, Ph. D. Thesis (1999), Polytechnic University.

6. Y. Pei, F.-B. Lin, R. L. Barbour, "Model-based imaging of scattering media using relative detector values," presented at 1999 OSA Annual Meeting & Exhibit: Optics in High-Tech Industries (Santa Clara, Calif., September 26–30).

7. J. Chang, H. L. Graber, R. L. Barbour and R. Aronson, "Recovery of optical cross-section perturbations in dense-scattering media by transport-theory-based imaging operators and steady-state simulated data," Appl. Opt. 35, 3963–3978 (1996)

8. P. E. Gill, W. Murray and M. H. Wright, Practical Optimization, Academic Press, New York (1981).

9. R. Aronson and N. Corngold, "Photon diffusion coefficient in an absorbing medium," J. Opt. Soc. Am. A 14, 262–266 (1997).

10. C. H. Schmitz, M. Löcker, J. Lasker, A. H. Hielscher, and R. L. Barbour, "Performance characteristics of silicon photodiode (SiPD) based instrument for fast function optical tomography," Proc. SPIE 4250, San Jose, Calif., in press, (2001).

11. S. Fantini, M. A. Franceschini, G. Gaida, H. Jess, H. Erdl, W. W. Mantulin, E. Gratton, K. T. Moesta, P. M. Schlag and M. Kaschke, "Contrast enhancement by edge effect corrections in frequency-domain optical mammography," in OSA Trends in Optics and Photonics on Advances in Optical Imaging and Photon Migration, R. R. Alfano and J. G. Fujimoto, eds., (Optical Society of America, Washington D.C., 1996, Vol. 2, pp. 160–163.

12. S. T. Flock, S. L. Jacques, B. C. Wilson, W. M. Star, and M. J. C. van Gemert, "Optical Properties of Intralipid: A phantom medium for light propagation studies," Lasers Surg. Med., Vol. 12, 510–519 (1992).

13. H. Dehghani, D. T. Delpy and S. R. Arridge, "Photon migration in non-scattering tissue and the effects on image reconstruction," Phys. Med. Biol. 44, 2897–2906 (1999).

14. R. L. Barbour, H. L. Graber, Y. Pei, S. Zhong, and C. H. Schmitz, "Optical tomographic imaging of dynamic features of dense scattering media," J. Opt. Soc. Am. A, in press (2001).

15. H. L. Graber, Y. Pei and R. L. Barbour, "Imaging of spatiotemporal coincident states by dynamic optical tomography," Proc. SPIE 4250, San Jose, Calif., in press, (2001).

16. G. Landis, S. Blattman, T. Panetta, C. H. Schmitz, H. L. Graber. Y. Pei, and R. L. Barbour, "Clinical applications of dynamic optical tomography in vascular disease," Proc. SPIE 4250, San Jose, Calif., in press, (2001).

17. N. Iftimia and H. Jiang, "Quantitative optical image reconstruction of turbid media by use of direct-current measurements," Appl. Opt. 39, 5256–5261, (2000).

18. Y. Xu, N. Iftimia, H. Jiang, L. Key, M. Bolster, "Imaging of in vitro and in vivo bones and joints with continuouswave diffuse optical tomography," Opt. Express 8, 447–451 (2001).
19. B. J. Hoenders, "Existence of invisible nonscattering objects and nonradiating sources," J. Opt. Soc. Am. A 14, 262–266, (1997).
20. A. H. Hielscher, R. E. Alcouffe, and R. L. Barbour, "Comparison of finite-difference transport and diffusion calculations for photon migration in homogeneous and heterogeneous tissues," Phys. Med. Biol. 43, 1285–1302 (1998).

What is claimed is:

1. A method for minimizing crosstalk in reconstructing the internal properties of a scattering medium, comprising:

generating a system of linear perturbation equations based on measured energy emerging from the scattering medium, the measured energy originating from a source and being measured by a detector, the linear perturbation equations having a weight matrix defining the influence that localized perturbations in a property of the scattering medium will have on the detector measurements;

scaling the weight matrix;

solving the system of linear perturbation equations for the localized perturbations in the property across the scattering medium, wherein positivity constraints are imposed on iteratively computed estimates of the localized property to obtain a positively constrained solution;

solving the system of linear perturbation equations for the localized perturbations in the property across the scattering medium, wherein negativity constraints are imposed on iteratively computed estimates of the localized property to obtain a negatively constrained solution; and summing the positively and negatively constrained solutions to obtain the localized perturbations in the property across the scattering medium.

2. The method of claim 1 wherein the linear perturbation equation is a perturbation formulation of the transport equation.

3. The method of claim 1 wherein the linear perturbation equation is a diffusion approximation to the transport equation.

4. The method of claim 1 wherein the linear perturbation equation is:

$$W_r^{(\mu_a)} \cdot \delta\mu_a + W_r^{(D)} \cdot \delta D = \delta u_r,$$

where $\delta\mu_a$ and $\delta D$ are vectors of localized differences in absorption and diffusion coefficients, respectively, between a target scattering medium and a reference scattering medium; $W_r^{(\mu_a)}$ and $W_r^{(D)}$ are weight matrices describing the influence that perturbations in the absorption and diffusion coefficients, respectively, of the reference medium have on detectors; and $\delta u_r$ is a vector of perturbations in detector readings.

5. The method of claim 4 wherein the properties of the reference medium are computed.

6. The method of claim 4 wherein the properties of the reference medium are measured.

7. The method of claim 4 wherein the perturbations in detector readings are relative detector readings.

8. The method of claim 7 wherein the relative detector readings are normalized differences between two sets of detector readings, defined by the equation:

$$(\delta u_r)_i = \left( \frac{(u_1)_i - (u_2)_i}{(u_2)_i} \right)(u_r)_i, \quad i = 1, 2, \ldots, M.$$

where, $u_r$ are the detector readings from the reference medium, $u_2$ and $u_1$ are two sets of measured data, and M is the number of unique source and detector combinations in the set of readings.

9. The method of claim 8 wherein the two sets of detector readings are a time average mean of readings over time and instantaneous readings at an instant in time.

10. The method of claim 1 wherein the properties are absorption and diffusion coefficients.

11. The method of claim 10 wherein the scaled weight matrix has the form, $W_r^{\%(k)} = W_r^{(k)} \cdot R^{(k)}$, where, k is one of the properties of the scattering medium, and $R^{(k)}$ is the scaled weight matrix whose entries are:

$$(R^{(k)})_{ij} = \begin{cases} \dfrac{1}{\frac{1}{M}\sum_{m=1}^{M} (W_r^{(k)})_{mj}} & j = 1, \\ & i, j = 1, 2, \ldots, N, \\ 0 & j \neq 1, \end{cases}$$

in which N is the number of elements used in discretizing the scattering medium having a domain $\Lambda$.

12. The method of claim 11 wherein the system of linear perturbation equations include an absorption coefficient weight matrix and a diffusion coefficient weight matrix.

13. The method of claim 1 wherein the positively and negatively constrained solutions are obtained using a conjugate gradient descent technique.

14. The method of claim 1 wherein the positively and negatively constrained solutions are obtained using a simultaneous algebraic reconstruction technique.

15. The method of claim 1 wherein the positively and negatively constrained solutions are obtained using a projection onto convex sets technique.

16. The method of claim 1 further comprising imposing a range constraint on at least on of the positively and negatively constrained solutions.

17. A method for minimizing crosstalk in reconstructing the internal properties of a scattering medium, comprising:

generating predicted detector readings for a reference medium;

generating at least one of an absorption and diffusion coefficient weight matrix defining the influence that localized perturbations in the coefficient of a reference medium have on surface detectors;

scaling the coefficient weight matrix;

generating a vector of detector normalized difference readings from a first vector and second vector of detector readings indicative of energy emerging from a target scattering medium, the emerging energy substantially originating from at least one source directing the energy into the target scattering medium;

generating at least one of an absorption coefficient system of linear perturbation equations and a diffusion coefficient system of linear perturbation equations wherein for the absorption coefficient equations the product of the absorption weight matrix and a perturbation in the absorption coefficient is equal to a corresponding perturbation in the normalized difference readings, and wherein for the diffusion coefficient equations the product of the diffusion weight matrix and a perturbation in the diffusion coefficient is equal to a corresponding perturbation in the normalized difference readings;

solving at least one of the generated systems of linear perturbation equations for a coefficient of the scattering medium, wherein positivity constraints are imposed on iteratively computed estimates of the coefficient to obtain a positively constrained solution;

solving at least one of the generated systems of linear perturbation equations for a coefficients of the scattering medium, wherein negativity constraints are imposed on iteratively computed estimates of the coefficient to obtain a negatively constrained solution; and summing the positively and negatively constrained solutions to obtain at least one of the coefficient of the scattering medium.

18. The method of claim 17 where the first and second vectors are two measured sets of data from a background and a target scattering medium, respectively.

19. The method of claim 17 where the first and second vectors are two measured sets of data from a time averaged mean and a specific point in time, respectively.

20. A method for minimizing crosstalk in reconstructing the internal properties of a scattering medium, comprising:

generating a system of linear perturbation equations based on measured energy emerging from the scattering medium, the measured energy originating from a source and being measured by a detector, the linear perturbation equations having a weight matrix defining the influence that localized perturbations in a property of the scattering medium will have on the detector measurements;

scaling the weight matrix;

solving the system of linear perturbation equations for the localized perturbations in the property across the scattering medium, wherein positivity constraints are imposed on iteratively computed estimates of the localized property to obtain a positively constrained solution; and solving the system of linear perturbation equations for the localized perturbations in the property across the scattering medium, wherein negativity constraints are imposed on iteratively computed estimates of the localized property to obtain a negatively constrained solution when the perturbations are know to be in a negative direction, and wherein positivity constraints are imposed on iteratively computed estimates of the localized property to obtain a positively constrained solution when the perturbations are know to be in a positive direction.

21. The method of claim 20 further comprising imposing a range constraint on at least on of the positively and negatively constrained solutions.

22. A system for minimizing crosstalk in reconstructing the internal properties of a scattering medium, comprising:

means for generating a system of linear perturbation equations based on measured energy emerging from the scattering medium, the measured energy originating from a source and being measured by a detector, the linear perturbation equations having a weight matrix defining the influence that localized perturbations in a property of the scattering medium will have on the detector measurements;

means for scaling the weight matrix;

means for solving the system of linear perturbation equations for the localized perturbations in the property across the scattering medium, wherein positivity constraints are imposed on iteratively computed estimates of the localized property to obtain a positively constrained solution;

means for solving the system of linear perturbation equations for the localized perturbations in the property across the scattering medium, wherein negativity constraints are imposed on iteratively computed estimates of the localized property to obtain a negatively constrained solution; and means for summing the positively and negatively constrained solutions to obtain the localized perturbations in the property across the scattering medium.

23. The system of claim 22 wherein the linear perturbation equation is a perturbation formulation of the transport equation.

24. The system of claim 22 wherein the linear perturbation equation is a diffusion approximation to the transport equation.

25. The system of claim 22 wherein the linear perturbation equation is:

$$W_r^{(\mu_a)} \cdot \delta\mu_a + W_r^{(D)} \cdot \delta D = \delta u_r,$$

where $\delta\mu_a$ and $\delta D$ are vectors of localized differences in absorption and diffusion coefficients, respectively, between a target scattering medium and a reference scattering medium; $W_r^{(\mu_a)}$ and $W_r^{(D)}$ are weight matrices describing the influence that perturbations in the absorption and diffusion coefficients, respectively, of the reference medium have on detectors; and $\delta u_r$ is a vector of perturbations in detector readings.

26. The system of claim 25 wherein the properties of the reference medium are computed.

27. The system of claim 25 wherein the properties of the reference medium are measured.

28. The system of claim 25 wherein the perturbations in detector readings are relative detector readings.

29. The system of claim 28 wherein the relative detector readings are normalized differences between two sets of detector readings, defined by the equation:

$$(\delta u_r)_i = \left( \frac{(u_1)_i - (u_2)_i}{(u_2)_i} \right)(u_r)_i, \quad i = 1, 2, \ldots, M.$$

where, $u_r$ are the detector readings from the reference medium, $u_2$ and $u_1$ are two sets of measured data, and M is the number of unique source and detector combinations in the set of readings.

30. The system of claim 29 wherein the two sets of detector readings are a time average mean of readings over time and instantaneous readings at an instant in time.

31. The system of claim 22 wherein the properties are absorption and diffusion coefficients.

32. The system of claim 31 wherein the scaled weight matrix has the form, $W_r^{\%(k)} = W_r^{(k)} \cdot R^{(k)}$, where, k is one of the properties of the scattering medium, and $R^{(k)}$ is the scaled weight matrix whose entries are:

$$(R^{(k)})_{ij} = \begin{cases} \dfrac{1}{\dfrac{1}{M}\sum_{m=1}^{M}(W_r^{(k)})_{mj}} & j = i, \\ 0 & j \neq i, \end{cases} \quad i, j = 1, 2, \ldots, N,$$

in which N is the number of elements used in discretizing the scattering medium having a domain $\Lambda$.

33. The system of claim 32 wherein the system of linear perturbation equations include an absorption coefficient weight matrix and a diffusion coefficient weight matrix.

34. The system of claim 22 wherein the positively and negatively constrained solutions are obtained using a conjugate gradient descent technique.

35. The system of claim 22 wherein the positively and negatively constrained solutions are obtained using a simultaneous algebraic reconstruction technique.

36. The system of claim 22 wherein the positively and negatively constrained solutions are obtained using a projection onto convex sets technique.

37. The system of claim 22 further comprising means for imposing a range constraint on at least on of the positively and negatively constrained solutions.

38. A system for minimizing crosstalk in reconstructing the internal properties of a scattering medium, comprising:

means for generating predicted detector readings for a reference medium;

means for generating at least one of an absorption and diffusion coefficient weight matrix defining the influence that localized perturbations in the coefficient of a reference medium have on surface detectors;

means for scaling the coefficient weight matrix;

means for generating a vector of detector normalized difference readings from a first vector and second vector of detector readings indicative of energy emerging from a target scattering medium, the emerging energy substantially originating from at least one source directing the energy into the target scattering medium;

means for generating at least one of an absorption coefficient system of linear perturbation equations and a diffusion coefficient system of linear perturbation equations wherein for the absorption coefficient equations the product of the absorption weight matrix and a perturbation in the absorption coefficient is equal to a corresponding perturbation in the normalized difference readings, and wherein for the diffusion coefficient equations the product of the diffusion weight matrix and a perturbation in the diffusion coefficient is equal to a corresponding perturbation in the normalized difference readings;

means for solving at least one of the generated systems of linear perturbation equations for a coefficient of the scattering medium, wherein positivity constraints are imposed on iteratively computed estimates of the coefficient to obtain a positively constrained solution;

means for solving at least one of the generated systems of linear perturbation equations for a coefficients of the scattering medium, wherein negativity constraints are imposed on iteratively computed estimates of the coefficient to obtain a negatively constrained solution; and means for summing the positively and negatively constrained solutions to obtain at least one of the coefficient of the scattering medium.

39. The system of claim 38 where the first and second vectors are two measured sets of data from a background and a target scattering medium, respectively.

40. The system of claim 38 where the first and second vectors are two measured sets of data from a time averaged mean and a specific point in time, respectively.

41. A system for minimizing crosstalk in reconstructing the internal properties of a scattering medium, comprising:

means for generating a system of linear, perturbation equations based on measured energy emerging from the scattering medium, the measured energy originating from a source and being measured by a detector, the linear perturbation equations having a weight matrix defining the influence that localized perturbations in a property of the scattering medium will have on the detector measurements;

means for scaling the weight matrix;

means for solving the system of linear perturbation equations for the localized perturbations in the property across the scattering medium, wherein positivity constraints are imposed on iteratively computed estimates of the localized property to obtain a positively constrained solution; and means for solving the system of linear perturbation equations for the localized perturbations in the property across the scattering medium, wherein negativity constraints are imposed on iteratively computed estimates of the localized property to obtain a negatively constrained solution when the perturbations are know to be in a negative direction, and wherein positivity constraints are imposed on iteratively computed estimates of the localized property to obtain a positively constrained solution when the perturbations are know to be in a positive direction.

42. The system of claim 21 further comprising means for imposing a range constraint on at least on of the positively and negatively constrained solutions.

* * * * *